(12) United States Patent
DiGiulio

(10) Patent No.: US 6,787,127 B2
(45) Date of Patent: Sep. 7, 2004

(54) COSMETIC COMPOSITION

(75) Inventor: Aristodemo C. DiGiulio, Fairfield, CT (US)

(73) Assignee: Medtech Products, Inc., Irvington, NY (US)

( * ) Notice: Subject to any disclaimer, the term of this patent is extended or adjusted under 35 U.S.C. 154(b) by 0 days.

(21) Appl. No.: 10/115,118

(22) Filed: Apr. 1, 2002

(65) Prior Publication Data

US 2003/0185775 A1 Oct. 2, 2003

(51) Int. Cl.[7] .............................. A61K 7/04; A61K 7/00
(52) U.S. Cl. .................... 424/61; 424/400; 424/401
(58) Field of Search ........................ 424/61, 400, 401; 134/38, 39; 510/118, 405, 407

(56) References Cited

U.S. PATENT DOCUMENTS

| | | | | |
|---|---|---|---|---|
| 5,342,536 A | * | 8/1994 | Miner et al. | 252/162 |
| 5,543,085 A | * | 8/1996 | Miner | 510/118 |
| 5,582,333 A | * | 12/1996 | Bennett | 222/546 |
| 6,225,269 B1 | * | 5/2001 | Baker | 510/118 |
| 6,503,488 B1 | * | 1/2003 | Rosen et al. | 424/65 |

* cited by examiner

*Primary Examiner*—Shelley A. Dodson
(74) *Attorney, Agent, or Firm*—Baker, Donelson, Bearman, Caldwell & Berkowitz

(57) ABSTRACT

A cosmetic composition for treating nails is provided to remove nail polish, to nourish and strengthen the nails and to moisturize and soften the cuticles around the nails.

9 Claims, No Drawings

US 6,787,127 B2

COSMETIC COMPOSITION

TECHNICAL FIELD

The present invention relates to a cosmetic composition. In a more specific aspect, this invention relates to a cosmetic composition for treating fingernails and toenails (sometimes collectively referred to in this application as "nails").

The present invention also provides a process for treating nails with a cosmetic composition.

BACKGROUND OF THE INVENTION

In the cosmetic industry of today, a multitude of compositions are commercially available to achieve various effects for the skin and face of a person.

Particularly, cosmetic compositions have been developed for a person's hands and feet, specifically the fingernails and toenails. These compositions are designed and formulated to provide color and other effects to the nails of a person's hands and feet. An example of a popular cosmetic composition in this area is nail polish, which is available in a wide variety of colors from clear to vividly intense shades.

Of course, the development of nail polish resulted in a need for a composition to remove the nail polish so that, for example, the color can be changed. In this way, different colors can be used for accents at various functions or for various purposes.

However, a disadvantage to nail polish removal compositions is that the use of such compositions may tend to weaken the nails. This potential disadvantage has lead to the development of compositions which are designed and formulated to nourish and strengthen nails and compositions which are designed and formulated to moisturize and soften cuticles. As these compositions, however, are separate from a nail polish remover composition, the user must purchase and apply these compositions in separate steps, which can result in a lengthy process.

In view of the above discussion, there is a need in the cosmetic industry for a composition which can be used, in a single step, (a) to remove nail polish, (b) to nourish and strengthen the nails to overcome any potential weakening of the nails by the nail polish remover composition and (c) to moisturize and soften the cuticles around the nails.

SUMMARY OF THE INVENTION

Briefly described, the present invention provides a cosmetic composition for treating nails. The composition of this invention provides for the removal of nail polish, for the nourishing and strengthening of the nails and for the moisturizing and softening of cuticles.

Accordingly, an object of this invention is to provide a cosmetic composition.

Another object of this invention is to provide a cosmetic composition which removes nail polish from fingernails and toenails.

Another object of this invention is to provide a cosmetic composition which nourishes nails.

Another object of this invention is to provide a cosmetic composition which strengthens nails.

Another object of this invention is to provide a cosmetic composition which moisturizes cuticles.

Another object of this invention is to provide a cosmetic composition which softens cuticles.

Still another object of this invention is to provide a cosmetic composition which can be applied as a liquid, cream, gel or other form.

Still another object of this invention is to provide a cosmetic composition which can be applied through a pad.

Still another object of this invention is to provide a cosmetic composition which can be applied as a liquid on a sponge positioned within a jar or other container.

These and other objects, features and advantages of this invention will become apparent from the following detailed description.

DETAILED DESCRIPTION OF THE INVENTION

In accordance with the present invention, nails are treated with a cosmetic composition which (a) removes nail polish, (b) nourishes and strengthens the nails and (c) moisturizes and softens the cuticles around the nails. This invention achieves these functions with a single composition. More than one application of the composition may be desired by the user, depending on the particular circumstances.

Specifically, the cosmetic composition of this invention is essentially comprised of water; a solvent component which breaks down the nail polish; a component which stabilizes the composition; a component which nourishes and strengthens the nails; and a component which moisturizes and softens the cuticles.

The cosmetic composition of this invention may be applied to the nails in a variety of forms, such as a liquid, cream, gel, through a pad or as a liquid contained in a sponge positioned within a jar or other container. A liquid form is preferred.

The process of this invention is practiced by applying the cosmetic composition to the nails with a brush, pad, cloth or other means of application (such as the above-described "sponge in a jar".

This composition contains water and a solvent component which is capable of breaking down the nail polish so that the polish can be removed. The term "breaking down" means that the bond between the polish and the nail is broken, which renders the polish removable. While many solvents can be used, preferred solvents are ethyl acetate, propylene carbonate, acetone, dimethyl ester or a mixture of two or more of these solvents. The solvent component is present in the range of about 40 to about 85, preferably about 45 to about 80, percent by weight.

The amount of water present in these compositions is from about 10 to about 25, preferably from about 15 to about 20, percent by weight.

A stabilizing component is used in the composition of this invention. Several stabilizing agents are effective, but the preferred agents are glycerin, propylene glycol, castor oil, isopropyl alcohol and specially denatured alcohols. A mixture of two or more of these agents can be used. The stabilizing component is generally used in amounts which range from about 1.0 to about 35, preferably about 2.0 to about 30.0, percent by weight.

Another essential component is one which moisturizes and softens the cuticle area around the nails. Preferred materials are glycerin, propylene glycol, castor oil or a mixture of two or more of these materials. This component is generally present in an amount of about 1.0 to about 5.0, preferably about 2.0 to about 3.0, percent by weight.

The component which serves to moisturize and soften the cuticles effectively prevents drying of the cuticles, adds back natural oils to the cuticles and softens the cuticles.

An essential component is a material which nourishes and strengthens the nails. Preferred materials are panthenol and vitamin E acetate oil, but other materials can be used. A mixture of two or more of these materials can also be used.

The nourishing and strengthening component is generally used in an amount from about 0.01 to about 0.5, preferably about 0.04 to about 0.4, percent by weight.

Certain components may provide more than one function in the composition of this invention. For example, glycerin, propylene glycol and castor oil can be used to provide a stabilizing effect and to moisturize and soften the cuticles.

Optionally, the cosmetic compositions of this invention may contain additional components to achieve different results. Examples of such optional components are fragrances, perfumes, pH adjusting agents (for example, citric acid), thickening agents (such as gelatin), colorants, co-solvents, etc. These optional components are used in varying amounts, as determined by the desired results in view of the other components.

Another optional component of this composition is a material which has a bitter or bad taste and, therefore, deters ingestion of the composition. Thus, this component adds a safety feature to the composition. A preferred material is a denatonium benzoate-alcohol solution. One or more of these materials can be used. This component can be present in an amount of about 0.0001 to about 0.05, preferably about 0.0005 to about 0.01, percent by weight.

The following are two especially preferred cosmetic compositions in accordance with the present invention.

Composition No. 1

| Component | Weight Percent Range |
| --- | --- |
| Ethyl Acetate | 35–55 |
| Specially Denatured Alcohol | 20–35 |
| Water | 15–25 |
| Propylene Carbonate | 1–5 |
| Dimethyl Ester | 1–4 |
| Glycerin | 0.5–1.5 |
| Fragrance | 0.1–1.5 |
| Propylene Glycol | 0.1–0.5 |
| Isopropyl Alcohol | 0.1–0.5 |
| Panthenol | 0.1–0.5 |
| Castor Oil | 0.01–0.1 |
| Denatonium Benzoate-Alcohol Solution | 0.0001–0.1 |
| Liquid Gelatin | 0.0001–0.01 |

Composition No. 2

| Component | Weight Percent Range |
| --- | --- |
| Acetone | 65–80 |
| Water | 15–25 |
| Propylene Carbonate | 1–5 |
| Glycerin | 1–4 |
| Dimethyl Ester | 1–4 |
| Propylene Glycol | 0.5–2 |
| Fragrance | 0.1–1.5 |
| Panthenol | 0.1–0.5 |
| Vitamin E Acetate Oil | 0.01–0.05 |
| Denatonium Benzoate-Alcohol Solution | 0.0001–0.1 |
| Citric Acid | 0.0001–0.01 |
| Liquid Gelatin | 0.0001–0.01 |

These two compositions provide excellent results in regard to the removal of nail polish, the nourishing and strengthening of the nails and the moisturizing and softening of the cuticles around the nails.

This invention has been described in detail with particular reference to certain embodiments, but variations and modifications can be made without departing from the spirit and scope of the invention as defined in the following claims.

What is claimed is:

1. A cosmetic composition for treating nails to remove nail polish, to nourish and strengthen the nails and to moisturize and soften cuticles, wherein the composition essentially comprises:

A. water;
   B. from about 40 to about 85 percent, by weight, of a solvent component which breaks down the nail polish, wherein the solvent component is ethyl acetate, propylene carbonate, acetone, dimethyl ester or a mixture of two or more of these solvents;
   C. from about 1.0 to about 35 percent, by weight, of a stabilizing component;
   D. from about 0.04 to about 0.5 percent, by weight, of a component which nourishes and strengthens the nails; and
   E. from about 1.0 to about 5.0 percent, by weight, of a component which moisturizes and softens cuticles around the nails.

2. A cosmetic composition as defined by claim 1 wherein the stabilizing component is glycerin, propylene glycol, castor oil, isopropyl alcohol, a specially denatured alcohol or a mixture of two or more of these materials.

3. A cosmetic composition as defined by claim 1 wherein the component which nourishes and strengthens is panthenol, vitamin E acetate or a mixture of these materials.

4. A cosmetic composition as defined by claim 1 wherein the component which moisturizes and softens is glycerin, propylene glycol, castor oil or a mixture of two or more of these materials.

5. A cosmetic composition for treating nails wherein the composition essentially comprises:

A. water;
   B. a solevent component which is a mixture of ethyl acetate, propylene carbonate and dimethyl ester;
   C. a stabilizing component which is a mixture of isopropyl alcohol, castor oil and a specially denatured alcohol;
   D. a nourishing and strengthening component which is a mixture of panthenol and vitamin E acetate oil; and
   E. a moisturizing and softening component which is a mixture of glycerin, propylene glycol and castor oil.

6. A cosmetic composition for treating nails, wherein the composition essentially comprises:

A. water;
   B. a solvent component which is a mixture of acetone, propylene carbonate and dimethyl ester,
   C. a stabilizing component which is a mixture of glycerin and propylene glycol;
   D. a nourishing and strengthening component which is a mixture of panthenol and vitamin E acetate oil; and
   E. a moisturizing and softening component which is a mixture of glycerin and propylene glycol.

7. A process for treating nails, wherein the process comprises applying to the nails a cosmetic composition as defined by claim 1.

8. A process for treating nails, wherein the process comprises applying to the nails a cosmetic composition as defined by claim 5.

9. A process for treating nails, wherein the process comprises applying to the nails a cosmetic composition as defined by claim 6.

* * * * *